US006667332B2

United States Patent
Li et al.

(10) Patent No.: US 6,667,332 B2
(45) Date of Patent: Dec. 23, 2003

(54) EFFICIENT PROCESS FOR THE PREPARATION OF A FACTOR XA INHIBITOR

(75) Inventors: Hui-Yin Li, Hockessin, DE (US); Luigi Anzalone, West Chester, PA (US); Fuqiang Jin, Wilmington, DE (US); David J. Meloni, New Castle, DE (US); Jung-Hui Sun, Hockessin, DE (US); Christopher A. Teleha, Bear, DE (US); Jia C. Zhou, Hockessin, DE (US); Thomas E. Smyser, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 13 days.

(21) Appl. No.: 09/960,040

(22) Filed: Sep. 21, 2001

(65) Prior Publication Data
US 2002/0061917 A1 May 23, 2002

Related U.S. Application Data
(60) Provisional application No. 60/234,622, filed on Sep. 22, 2000.

(51) Int. Cl.[7] .............................................. A61K 31/423
(52) U.S. Cl. ........................................ 514/379; 548/241
(58) Field of Search ........................... 548/241; 514/379

(56) References Cited

U.S. PATENT DOCUMENTS 6,339,099 B1 * 1/2002 Lam et al. .................. 514/378

FOREIGN PATENT DOCUMENTS

WO          9857951         12/1998

* cited by examiner

*Primary Examiner*—Joseph K. McKane
*Assistant Examiner*—Rebecca Anderson
(74) *Attorney, Agent, or Firm*—David H. Vance

(57) ABSTRACT

The present invention relates to the process for the preparation of the compound of Formula I:

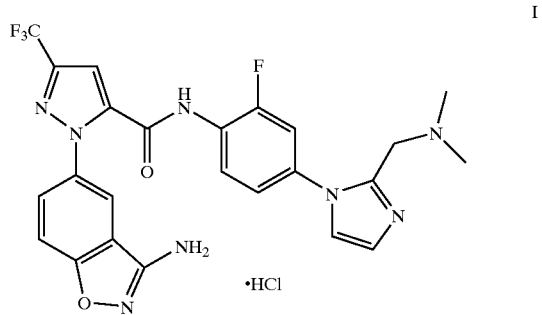

from its corresponding 3-cyano-4-fluorophenyl-pyrazole and intermediates useful therein.

35 Claims, No Drawings

EFFICIENT PROCESS FOR THE PREPARATION OF A FACTOR XA INHIBITOR

FIELD OF THE INVENTION

This invention relates generally to an efficient process for the preparation of a benzisoxazolyl-pyrazole. Benzisoxazolyl-pyrazoles are useful as factor Xa inhibitors.

BACKGROUND OF THE INVENTION

Factor Xa inhibitors like those of Formula Ia shown below:

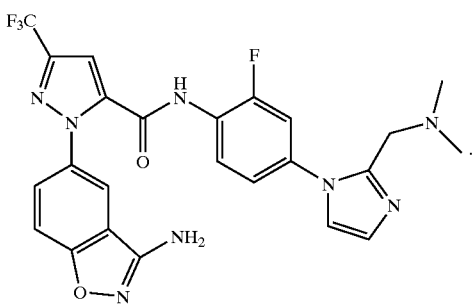

Ia

WO98/57951 describes the synthesis of the compound of Formula Ia, as its trifluoroacetic acid salt, as follows:

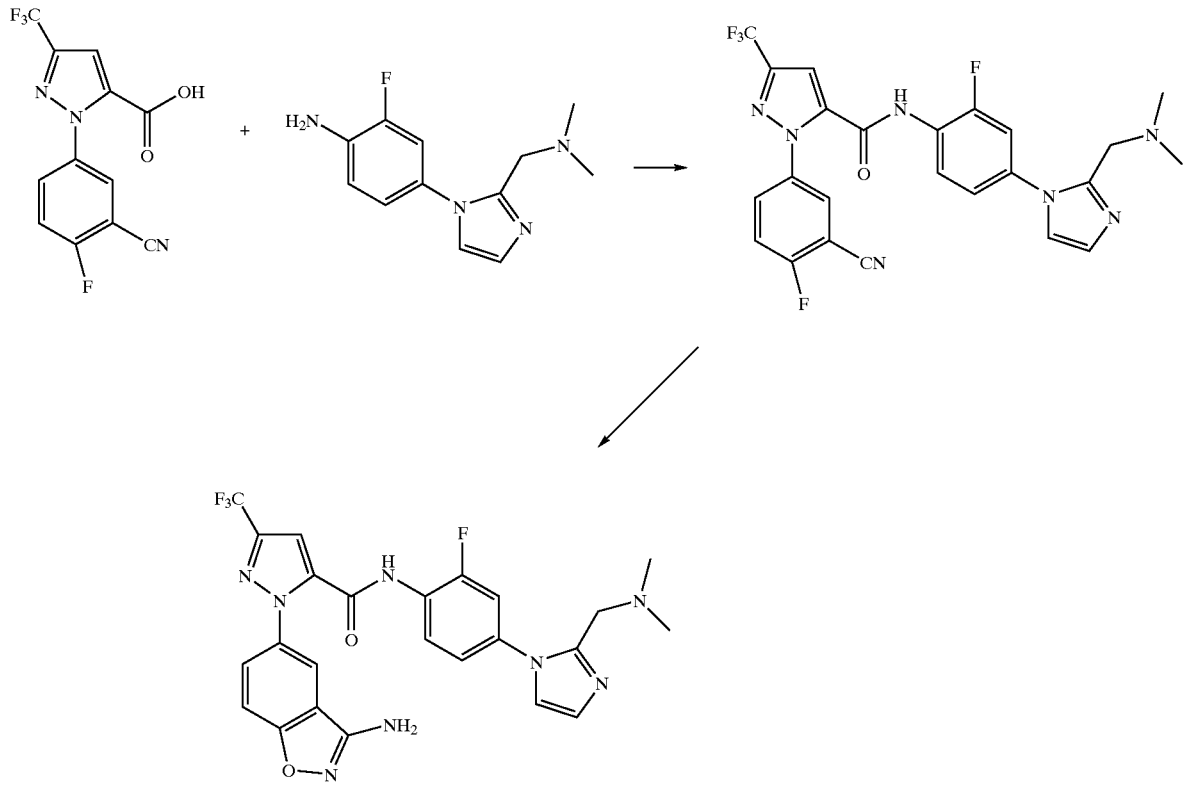

In the above procedure, the pyrazole carboxylic acid and aniline are coupled and isolated as a free base. The 3-cyano-4-fluorophenyl group of the resulting product is then converted to 1-aminobenzisoxazole. One problem with this procedure is that the acid-aniline coupling product is difficult to purify. A second problem is that the conversion to the 1-aminobenzisoxazole moiety requires the presence of a strong, expensive base such as KOt-Bu.

It can be seen that the preparation of a compound of Formula I is difficult. Thus, it is desirable to find an efficient synthesis of such a compound.

SUMMARY OF THE INVENTION

Accordingly, one object of the present invention is to provide a novel process for preparing a compound of Formula I.

It is another object of the present invention to provide intermediates that are useful in preparing a compound of Formula I.

It is another object of the present invention to provide novel salt, crystalline, and solvent forms of Formula I.

It is another object of the present invention to provide pharmaceutical compositions comprising a pharmaceutically acceptable carrier and a therapeutically effective amount of at least one of the compounds of the present invention or a pharmaceutically acceptable salt thereof.

It is another object of the present invention to provide a method for treating thromboembolic disorders comprising administering to a host in need of such treatment a therapeutically effective amount of at least one of the compounds of the present invention or a pharmaceutically acceptable salt thereof.

It is another object of the present invention to provide novel compounds for use in therapy.

It is another object of the present invention to provide the use of novel compounds for the manufacture of a medicament for the treatment of a thromboembolic disorder.

DETAILED DESCRIPTION OF PREFERRED EMBODIMENTS

Thus, in an embodiment, the present invention provides a novel process for making a compound of Formula I:

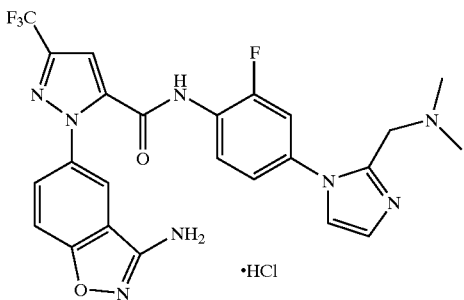

I comprising:

(c) contacting a compound of Formula IVa with maleic acid to form a compound of Formula IV;

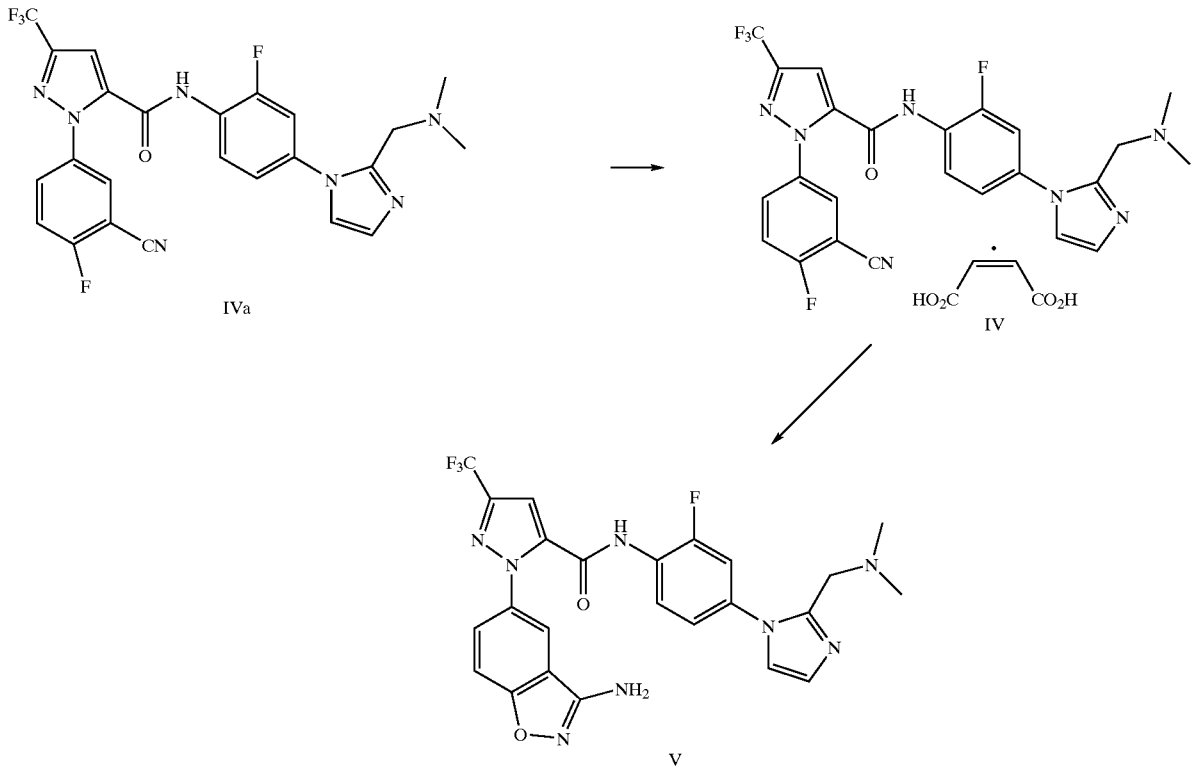

(d) converting a compound of Formula IV to a compound of Formula V; and, (e) forming a compound of Formula I.

In a preferred embodiment, in (c), contacting with maleic acid is performed in the presence of a first solvent, ethyl acetate.

In another preferred embodiment, in (c), a second solvent, 1-chlorobutane, is added to enhance precipitation.

In another preferred embodiment, (d) is performed by contacting a compound of Formula IV with HONHCOCH$_3$ in the presence of a base and a solvent.

In another preferred embodiment, the base is selected from K$_2$CO$_3$, Na$_2$CO$_3$, KHCO$_3$, NaHCO$_3$, KF, NaOH, and KOH.

In another preferred embodiment, the base is K$_2$CO$_3$.

In another preferred embodiment, in (d), the solvent is selected from DMSO, DMAC, N-methylpyrrolidinone, and DMF.

In another preferred embodiment, in (d), the solvent is DMF, comprising: 0.5 to 50% by volume of water.

In another preferred embodiment, in (d), the solvent is DMF, comprising: 10, 11, 12, 13, 14, to 15% by volume of water.

In another preferred embodiment, in (d), the solvent is DMF, comprising: 15% by volume of water.

In another preferred embodiment, (e) is performed by contacting a compound of Formula V with HCl in a solvent selected from methanol, acetonitrile, isopropyl alcohol, ethanol, propanol, acetone, methyl isobutyl ketone (MIBK), 2-butanone, and water.

In another preferred embodiment, (e) is performed by contacting a compound of Formula V with HCl in ethanol.

In another preferred embodiment, the compound of Formula I is a mono-HCl salt.

In another preferred embodiment, the compound of Formula I is crystalline.

In another preferred embodiment, the compound of Formula I is a solvate selected from ethanol, propanol, isopropanol, acetone, MIBK, 2-butanone, and water.

In a more preferred embodiment, the compound of Formula I is an ethanol solvate.

In another embodiment, the present invention provides a novel process for making a compound of Formula IVa:

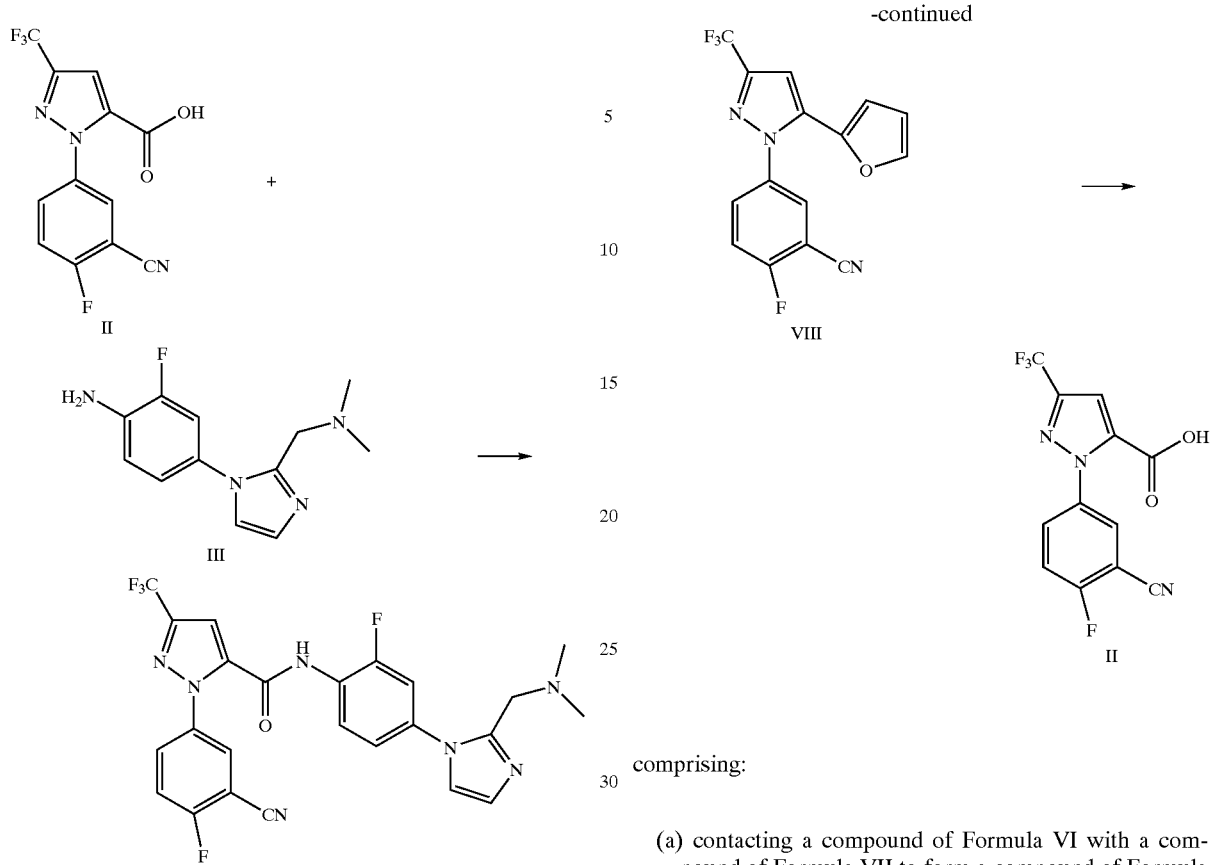

comprising:

(b) coupling compounds of Formulas II and III to form a compound of Formula IVa.

In another preferred embodiment, the compound of Formula IVa is used without purification in (c).

In another preferred embodiment, (b) is performed by contacting a compound of Formula II with an acid activator, in a solvent and a first base, followed by contacting the resulting solution with a compound of Formula III.

In another preferred embodiment, (b) is performed by contacting a compound of Formula II with oxalyl chloride in acetonitrile and pyridine, followed by contacting the resulting solution with a compound of Formula III.

In another preferred embodiment, after a compound of Formula II has been contacted with a compound of Formula III, a second base is added to the reaction solution.

In another preferred embodiment, the second base is diisopropylethylamine.

In another embodiment, the present invention provides a novel process for making a compound of Formula II:

comprising:

(a) contacting a compound of Formula VI with a compound of Formula VII to form a compound of Formula VIII; and, (a₁) converting a compound of Formula VIII to a compound of Formula II.

In another embodiment, the present invention provides a novel compound of Formula I:

wherein I is a mono-HCl salt.

In another preferred embodiment, the compound of Formula I is crystalline.

In another preferred embodiment, the compound of Formula I is an ethanol solvate.

In another embodiment, the present invention provides a novel compound of Formula IV:

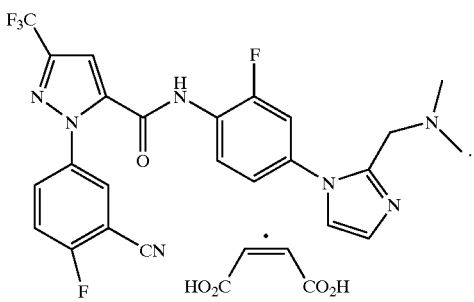

IV

In another embodiment, the present invention provides a novel compound of Formula Va:

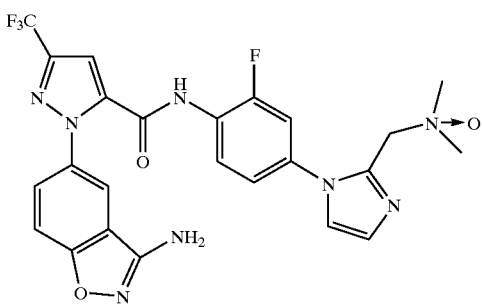

Va or a pharmaceutically acceptable salt form thereof.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides novel method for treating a thromboembolic disorder, comprising: administering to a patient in need thereof a therapeutically effective amount of a compound of the present invention or a pharmaceutically acceptable salt form thereof.

In another embodiment, the present invention provides a compound of the present invention for use in therapy.

In another embodiment, the present invention provides the use of a compound of the present invention for the manufacture of a medicament for the treatment of a thromboembolic disorder.

DEFINITIONS

As used herein, the following terms and expressions have the indicated meanings. It will be appreciated that the compounds of the present invention may contain an asymmetrically substituted carbon atom, and may be isolated in optically active or racemic forms. It is well known in the art how to prepare optically active forms, such as by resolution of racemic forms or by synthesis from optically active starting materials. All chiral, diastereomeric, and racemic forms and all geometric isomeric forms of a structure are intended, unless the specific stereochemistry or isomer form is specifically indicated.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The term "substituted," as used herein, means that any one or more hydrogens on the designated atom are replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The reactions of the synthetic methods claimed herein may be preferably carried out in the presence of a base, the base being any of a variety of bases, the presence of which in the reaction facilitates the synthesis of the desired product. Suitable bases may be selected by one of skill in the art of organic synthesis. Suitable bases include, but are not limited to, inorganic bases including, but not limited to, alkali metal, alkali earth metal, thallium, and ammonium hydroxides, alkoxides, phosphates, and carbonates, including, but not limited to, sodium hydroxide, potassium hydroxide, sodium carbonate, potassium carbonate, cesium carbonate, thallium hydroxide, thallium carbonate, tetra-n-butylammonium carbonate, and ammonium hydroxide.

The reactions of the synthetic methods claimed herein may be carried out in solvents that may be readily selected by one of skill in the art of organic synthesis, the solvents generally are any one that is substantially non-reactive with the starting materials (reactants), intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups including, but not limited to, amines, and alkali or organic salts of acidic groups including, but not limited to, carboxylic acids. The pharmaceutically acceptable salts include conventional non-toxic salts or quaternary ammonium salts of the parent compound formed, for example, from non-toxic inorganic or organic acids. For example, conventional non-toxic salts include those derived from inorganic acids including, but not limited to, hydrochloric, hydrobromic, sulfuric, sulfamic, phosphoric, and nitric; and the salts prepared from organic acids including, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile is preferred. Lists of suitable salts are found in *Remington's Pharmaceutical Sciences*, 17th ed., Mack Publishing Company, Easton, Pa., 1985, p. 1418, the disclosure of which is hereby incorporated by reference.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

SYNTHESIS

The processes of the present invention can be practiced in a number of ways depending on the solvent, base, and temperature chosen. As one of ordinary skill in the art of organic synthesis recognizes, the time for reaction to run to completion as well as yield will be dependent upon all of the variables selected. The following schemes show a representation of the overall sequence of the present invention.

Preparation of Formula VIII

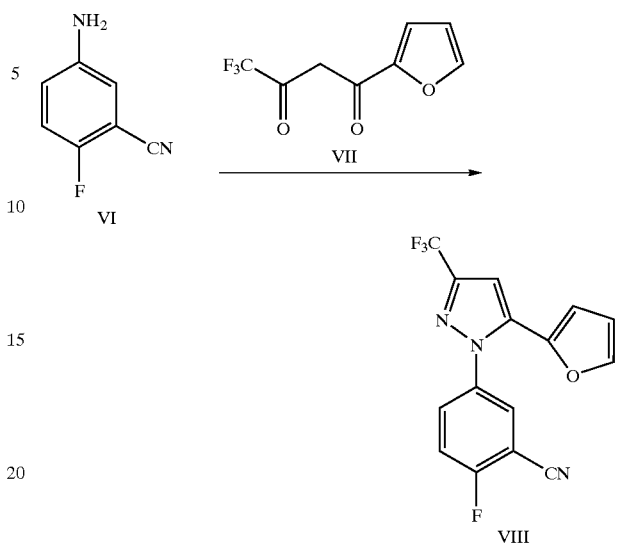

VI can be converted to VIII by a novel hydrazine in-situ trapping procedure. The hydrazine intermediate can be prepared by treating VI with HCl and $NaNO_2$. Preferably, VI is added to a cooled (e.g., $-10$ to $-5°$ C.) solution of HCl. The $NaNO_2$ can then added and the solution preferably maintained at a temperature of from $0$–$10°$ C. At this point, AcOH can be added to the solution. $SnCl_2 \cdot 2H_2O$ can then be added to complete formation of the hydrazine. The resulting product may be isolated or used in situ. Preferably, it is used in situ.

VIII can then be formed by addition of VII to the newly formed hydrazine. This addition is preferably performed in the presence of MeOH and at a temperature of from $35$–$55°$ C.

Preparation of Formula II

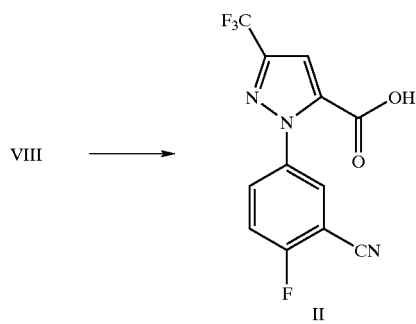

Oxidation of VIII should provide II. The oxidation is performed by contacting VIII with an oxidant in the presence of a solvent and optionally a buffer.

One of ordinary skill in the art would recognize that oxidants such as $KMnO_4$ or $NaClO_2$ can be used. Preferably, $KMnO_4$, in the presence of a buffer, is used as the oxidant. VIII can be suspended in an alcoholic solvent (e.g., t-butyl alcohol). The suspension is preferably maintained at a temperature of from $35$–$50°$ C. An aqueous solution of a buffer known to those of skill in the art (e.g., monobasic sodium phosphate monohydrate) can then be added. Preferably, the buffer is about 0.5 to 4N. Aqueous $KMnO_4$ can then be added to the reaction solution. After the reaction is complete, II can be isolated.

Preparation of Formula IVa

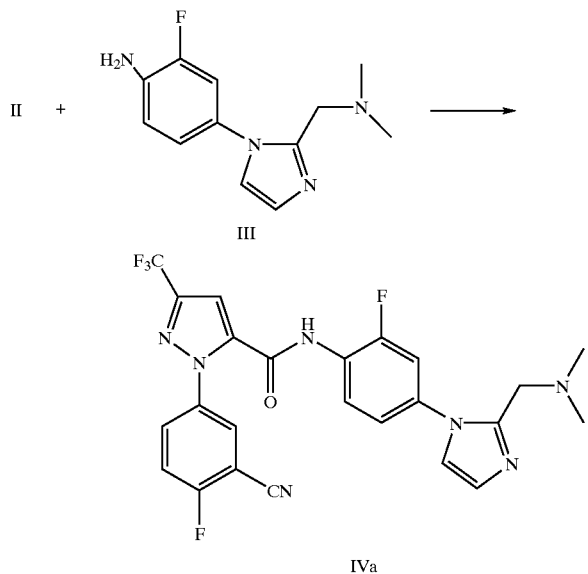

IVa can be formed by coupling II and III. The coupling is preferably performed by contacting II with an acid activator, in a solvent and in the presence of a base, followed by contacting the resulting solution with III. An acid activator like thionyl chloride or oxalyl chloride can be used, with oxalyl chloride being a preferred activator. The addition of the acid activator is preferably performed at a temperature of from 10–30° C.

Contacting II and oxalyl chloride can be performed in a solvent selected from acetonitrile, THF, and methylene chloride, with acetonitrile being preferred. The first base can be selected from DMAP, triethylamine, diisopropylethylamine, N-methyl morpholine, and pyridine, with pyridine being preferred. The amount of first base present is preferably from 0.2 to 1 molar equivalent based on II, more preferably it is 0.4 molar equivalents.

The desired amount of oxalyl chloride to be added will be based on the amount of II present in the solution and the amount of water present in the solution. The amount of water present can be determined by known means, such as the Karl Fischer titration. Preferably, the number of moles of oxalyl chloride added is equal to or slightly greater than the sum of the number of moles of II and water present.

Once II has been activated, it can be contacted with III. Preferably, the reaction mixture is cooled to from 0–10° C. prior to contacting with III. After contacting III with the reaction mixture, a second base is preferably added. The second base can be selected from diisopropylethylamine, pyridine, DMAP, triethylamine, and N-methyl morpholine, with diisopropylethylamine being preferred. The amount of second base present is preferably from about 1–3 molar equivalents, more preferably about 2.2 molar equivalents based on the amount of II present.

Preparation of Formula IV

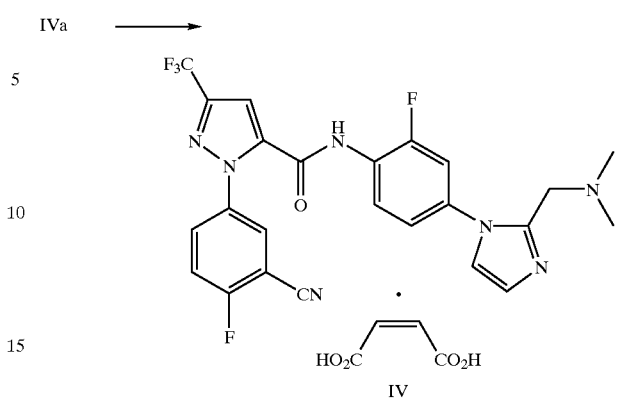

IV can be formed from IVa with or without purification of IVa. Preferably, IV is formed from IVa without purification. IVa is usually isolated as an oily substance. IVa is preferably taken up in a first solvent and maleic acid is added. To this solution can be added a second solvent to enhance or accelerate precipitation of IV. Preferably from 0.9 to 1.1 molar equivalents of maleic acid are present based on the amount of II present, more preferably about 0.95 molar equivalents. The first solvent can be selected from the group acetone, chloroform, ethyl acetate MIBK, i-propyl acetate, i-propyl alcohol, and THF, and is preferably ethyl acetate. The second solvent can be selected from the group 1-chlorobutane, heptane, hexane, methylene chloride, and TBME, and is preferably 1-chlorobutane. Preferably, this reaction is run at about room temperature.

Preparation of Formula V

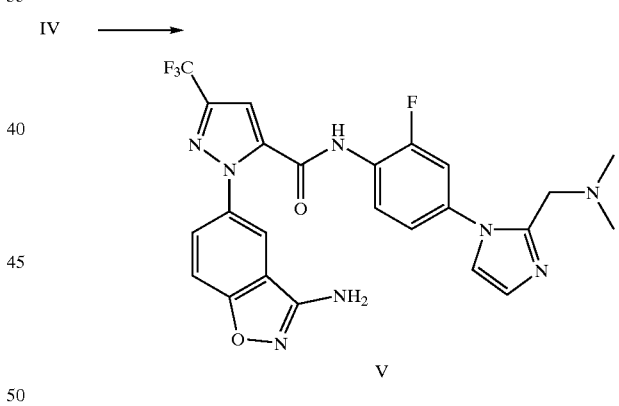

V can be prepared by contacting IV with $HONHCOCH_3$ in the presence of a base and a solvent. Preferably, the base is selected from $K_2CO_3$, $Na_2CO_3$, $KHCO_3$, $NaHCO_3$, KF, NaOH, and KOH, with $K_2CO_3$ being a more preferred base. The solvent may be selected from DMSO, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), and N-methylpyrrolidinone (NMP). A preferred solvent is DMF. It is preferred that the DMF comprises 0.5 to 50% by volume of water, more preferably, 0.5, 1, 2, 3, 4, 5, 6, 7, 8, 9, 10, 11, 12, 13, 14, to 15% by volume of water, even more preferably 10, 11, 12, 13, 14, to 15% by volume of water, and still more preferably 15% by volume of water.

Preferably, $HONHCOCH_3$, DMF, and $K_2CO_3$ are mixed together followed by contacting with water. This reaction mixture is preferably kept at about 20–30° C. Upon contacting of the reaction mixture with IV, the reaction is preferably stirred at about room temperature.

Preparation of Formula I

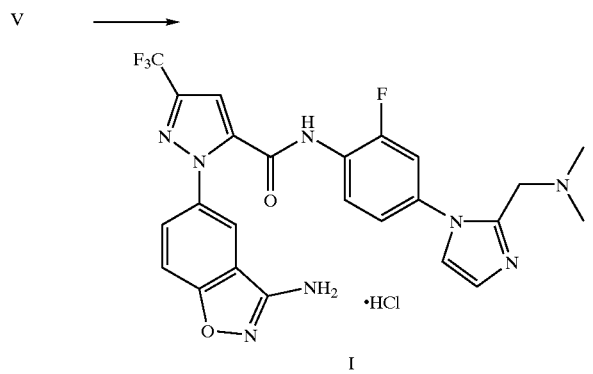

I can be formed from V by dissolving V in a solvent and contacting this solution with HCl. Preferably, the solvent is selected from methanol, acetonitrile, isopropyl alcohol, ethanol, propanol, acetone, methyl isobutyl ketone (MIBK), 2-butanone, and water, with ethanol being a more preferred solvent. V is preferably taken up in a solvent (e.g., ethanol) at a temperature of from 60–80° C. HCl is preferably contacted with the solution that is at a temperature of from 20–40° C. Preferably, the HCl is in an alcoholic solution. The alcoholic solution is preferably i-propyl alcohol.

I preferably precipitates from the reaction mixture. This precipitation can be enhanced by cooling the mixture to a temperature of about 0–10° C. Preferably I is a crystalline mono-HCl salt. More preferably, I is a solvate selected from ethanol, propanol, isopropanol, acetone, MIBK, 2-butanone, and water. Even more preferably, I is an ethanol solvate.

Other features of the invention will become apparent in the course of the following descriptions of exemplary embodiments that are given for illustration of the invention and are not intended to be limiting thereof.

EXAMPLES

Example 1

Preparation of VIII

To a 40 L Hastelloy "C" reactor fitted with an overhead air stirrer, thermocouple, condenser and nitrogen inlet, was charged conc. HCl (5.5 L). The reactor was cooled to between −5 and −10° C. VI (tan solid, 726 g, 5.3 mol) was added over 12 minutes while maintaining the internal temperature between −5 and −7° C. An additional 500 mL of conc. HCl was used to rinse down any VI hung up on the walls of the reactor. The resulting tan slurry was maintained at −5° C. over the next 10 minutes while a solution of sodium nitrite (450 g, 6.5 mol) in 3.1 L of purified water was prepared. The first 1500 mL of the sodium nitrite solution was added over 20 minutes wherein the internal temperature rose to 10° C. The addition was stopped for 30 minutes in order for the internal temperature to cool down and equilibrate to 2–3° C. The addition of sodium nitrite solution was resumed and the remaining 1.7 L was added over 30 minutes, while maintaining a temperature of 5–7° C. The batch was agitated for an additional 30 minutes at 6° C. Acetic acid (1.8 L) was added in one bolus with no appreciable change in the internal temperature (6° C.). A solution of $SnCl_2 \cdot 2H_2O$ (2.8 kg, 12.2 mol) was prepared in 1.9 L $H_2O$ and 1.9 L of conc. HCl and added to the reaction over 55 minutes while maintaining the temperature between 6–10° C. The resulting white "milkshake-like" slurry was agitated for an additional 30 minutes.

Methanol (10 L) was charged as one bolus into the reactor and the reaction mixture was heated to 40° C. A solution of 4,4,4-trifluoro-2-furyl-1,3-butanedione (VII, 830 mL, 1.2 kg, 5.6 mol) in 3.1 L of MeOH was added over 35 minutes while maintaining an internal temperature between 41–43° C. After addition was complete, the batch was held between 45–50° C. for an additional 1.5 h whereupon the heat was shut off and the resulting orange slurry was allowed to cool to ambient temperature overnight (16 h) under a nitrogen atmosphere. The next morning, the batch was cooled further to help promote precipitation of VIII. The batch was cooled down to 0° C. and held for 1 hour at 0° C. before dropping the slurry onto a Dacron filter cloth in a 32 cm Buchner funnel. The filtration took 1 hour and the cake depth was determined to be 3.5 cm. The cake was rinsed with 3 L of cold (0–5° C.) 50/50 isopropanol/water followed by 2.9 L of water. The wet cake (3.4 kg) was dried to constant weight in a vacuum oven at 45° C. and 22 mm Hg over the weekend to produce 1.3 Kg of VIII as a yellow solid (1.3 Kg, 94.5 wt %, 71.7% corrected yield).

Example 2

Preparation of II

A 50 L Hastelloy C reactor, equipped with an overhead air stirrer, a thermocouple, an addition funnel, a condenser, and a nitrogen inlet was charged with melted t-butyl alcohol (10 L), followed by solid VIII (1160 g). An additional quantity of t-butyl alcohol (4.5 L) was used for purposes of rinsing the original containers and was added to the reactor. The suspension was warmed to between 38° C. and 45° C. until a homogeneous solution resulted. An aqueous solution of monobasic sodium phosphate monohydrate (1245 g in 5.2 L of purified water) was added to the mixture over approx. 15 min between 35° C. and 45° C. Celite® 545 (3.2 Kg) was added to the reactor between 38° C. and 45° C. and stirring was maintained to insure even dispersion of the solid. A commercial 40% aqueous solution of sodium permanganate (5.76 L) was added slowly over approx. 2.5 h, maintaining an internal temperature range between 42° C. and 50° C. The reaction mass was allowed to cool to ambient temperature and was held overnight with continuous stirring.

The next morning, the mixture was again heated to between 45° C. and 50° C. and t-butyl methyl ether (6.0 L) was added, followed by solid Celite® 545 (3.2 Kg) and neutral alumina (4.15 Kg). The mixture was stirred for approx. 15 min, filtered, and the cake was rinsed with t-butyl methyl ether (6 L total rinse volume). All filtrates obtained were recombined and the solvents were removed by distillation. When the distillation had ceased, purified water (5 L) was added, followed by a second distillation. The clear, homogeneous residue was diluted with water to give 18 L of total solution. n-Chlorobutane (8 L) was added, the biphasic mixture was slowly stirred for 15 min, and the upper layer was separated and discarded. The weakly basic aqueous layer was cooled to between 3° C. and 7° C. and 30% aqueous citric acid solution (3.3 L) was added, whereupon the crude II precipitated. The solids were collected by filtration and the cake was rinsed with purified water (5.0 L total rinse volume). Wet, yellow II was packed out and dried to constant weight in a vacuum oven at 70° C., affording dry II (815.1 g; 98.8 wt-%, 75% yield).

Example 3

Preparation of III

III can be prepared in accordance with the procedure described in co-pending U.S. Provisional Patent Application 60/220932, filed Jul. 26, 2000, the contents of which are hereby incorporated by reference. The following is an example of the preparation of III.

Dimethylamine in THF (7.2 L of 2.0 M solution, 14.3 mol) was charged into a 5 gallon Parr hydrogenator. 2-Formyl-imidazolyl (1.25 kg, 13.0 mol) and methanol (2.4 L) was charged next. After pressure testing the system with nitrogen, Pd/C (10%) (125 g, containing approximately 50% by weight water) was charged. Jacket cooling was set at 25° C. The batch was then pressurized with hydrogen and the pressure was maintained in the range 50–60 psig. The first 20 minutes of reaction saw a rise in the internal temperature to 35° C. and hydrogen uptake was extremely rapid. For the next 2 hours before the hydrogen pressure was released, the internal temperature was 30–31° C. HPLC analysis indicated that the conversion to 2-(N,N-dimethylaminomethyl) imidazole was complete (remaining 2-formyl-imidazolyl A% <2% versus 2-(N,N-dimethylaminomethyl)imidazole >98%). The batch was filtered through a 0.5 micron cartridge filter and then through a 0.45 micron minifilter to remove Pd/C. A solution of 1/1 v/v MeOH/THF (5 L) was used to wash out the reactor and line and was directed via the cartridge filters to the carboy containing the rest of the filtrate. The combined filtrates were concentrated via rotary evaporator to a 2.3 kg solution (contained 1.6 Kg of 2-(N,N-dimethylaminomethyl)imidazole), which was then used directly for next step.

To each of two 22 L five neck round bottom flasks equipped with over head air stirrer, thermocouple, and distillation set-up with nitrogen cap was charged a solution of crude 2-(N,N-dimethylaminomethyl)imidazole (4.86 kg of a solution made by the above procedure that contained 3.0 Kg of 2-(N,N-dimethylaminomethyl)imidazole). To each of the two reactors, anhydrous DMSO (10.0 L) was then introduced to give a dark amber clear solution. The residual MeOH and THF from the crude 2-(N,N-dimethylaminomethyl)imidazole in each of the two reactors was subsequently distilled off in vacuo at 50–60° C. before 1- amino-2-fluoro-4-iodobenzene (2.15 Kg, 9.05 mole) and powdered $K_2CO_3$ (2.5 Kg, 18.1 mole, 2.0 equiv) were added to each of the two reactors at 40–50° C., respectively. Each of the two reactors was then degassed three times with a vacuum/nitrogen cycle ending on nitrogen before being charged with powdered CuI (260 g, 1.35 mole, 0.15 equiv). The resulting reaction mixture in each of the two reactors was degassed three times again with a vacuum/nitrogen cycle ending on nitrogen before being warmed to 125–130° C.

When the reaction was deemed complete after 16 h at 125–130° C. (1- amino-2-fluoro-4-iodobenzene<5% at 254 nm via HPLC analysis), the reaction mixture in each of the two reactors was cooled to 40–50° C. To each of the two reactors was added 4.0 L of saturated $NH_4Cl$ aqueous solution, and the resulting mixture was agitated for 1 h at 20–25° C. The mixture was then filtered through a Celite® bed, and each of the two reactors was washed with 1.0 L of saturated $NH_4Cl$ aqueous solution and 8.5 L of ethyl acetate. Half of the combined filtrates and washing solution were sequentially poured into a 40 L reactor, and the mixture was agitated at 20–25° C. for 0.5 h before the two layers were separated. The combined aqueous layers were poured back into the 40 L reactor and were extracted with ethyl acetate (4×15 L). During the process of the organic solvent extraction, emulsion colloid was resolved by filtration of the mixture through a Celite® bed before the two layers were separated. The combined organic extracts were then washed with 6.0 L of saturated $NH_4Cl$ aqueous solution, dried over $MgSO_4$ (2.0 Kg), and decolorized over active carbon (charcoal, 500 g) at 20–25° C. for 1 h in two separate 22 L reactors. The mixture was filtered through a Celite® bed, and each of the reactors was washed with ethyl acetate (2 L). The combined organic filtrates were then poured into a 40 L reactor, and a total of 68 L of ethyl acetate were successively distilled off in vacuo at 45–50° C. The residual slurry of the crude III in 9.0 L of ethyl acetate was subsequently transferred into a 22 L reactor, and the mixture was warmed to reflux (77–78° C.) to give a brown to black solution. Heptanes (6.0 L) were then added to the solution at 70° C., and the solution was cooled to 45–50° C. before being treated with active carbon (charcoal, 400 g). The mixture was warmed to reflux again for 1 h before being filtered through a Celite® bed at 50–55° C. The Celite® bed was washed with 2.0 L of ethyl acetate, and the combined filtrates and washing solution were poured back into a clean 22 L reactor. A total of 5.0 L of ethyl acetate was distilled off in vacuo at 45–50° C., and an additional 5.0 L of heptanes were added into the reactor at 50° C. The mixture was then gradually cooled to 20–25° C. and stirred at 20–25° C. for 1 h before being cooled to 5–10° C. for 2 h to precipitate III. The solids were collected by filtration on a 27 cm porcelain funnel lined with Dacron® cloth and washed with 20% (v/v) of TBME/heptanes (2×2.5 L). The solids were dried in vacuo with nitrogen purge at 40–45° C. to a constant weight. The first crop of III (1.749 Kg, 4.235 Kg theoretical, 41.3%) was obtained as pale-yellow crystals.

The combined mother liquor and washing solution was then concentrated in vacuo to afford the second crop of III (500 g, 4.235 kg theoretical, 11.8%; a total of 53.1% yield) as pale-yellow crystals.

Example 4

Preparation of IVa and IV

II (781 g, 2.61 mol) was combined with acetonitrile (11.3 L). The amount of water present in the solution was determined by performing a Karl Fischer titration. The volume of oxalyl chloride to be charged was calculated by adding the moles of II plus moles of water determined to be present to give moles of oxalyl chloride. Pyridine (81 mL, 1.0 mol) was charged followed by oxalyl chloride (227 mL, 2.60 mol). The reaction was warmed to 55–60° C. and held at that temperature for 1 hour. The progress of the reaction was followed by drawing a sample and quenching into $NH_4OH$. Once the reaction was considered complete, a vacuum distillation was performed to remove 12% (v/v) of the solvent. Following the distillation fresh acetonitrile was added back to the reaction to replace the volume removed by the distillation.

The reaction mixture was chilled to 5° C. followed by the addition of III (598 g, 2.55 mol). An exotherm of 12° C. accompanied the addition. After allowing the solution to return to 5° C., diisopropylethylamine (975 mL, 5.60 mol) was added to the reaction over 60 minutes via addition funnel. Following the addition, the cooling bath was removed and the reaction was allowed to return to room temperature. Two hours following the addition of base the reaction was complete. The reaction was diluted with EtOAc (12 L) and washed with water (2×8 L). The aqueous washes were combined and back extracted with EtOAc (1×8 L). The organic fractions were combined and dried over $MgSO_4$, filtered and concentrated to yield a brown oil, IVa.

The oil was reconstituted with EtOAc (11.3 L) and transferred to a 40 L kettle. Maleic acid (290 g, 2.50 mol) was added to the EtOAc solution that was then stirred at room temperature for 60 minutes. Approximately 15 minutes after the addition of maleic acid the resulting salt, IV, began to precipitate out of solution. 1-Chlorobutane (24 L) was added over 60–90 minutes to ensure complete precipitation. Following the addition of 1-chlorobutane, the IV solution was stirred at room temperature for 3 h. The salt was isolated by filtration and washed with 1-chlorobutane (6 L). The solids were dried in a 75° C. vacuum oven to constant weight to give 1.49 Kg (100.7 wt.%, 94.1% yield) of IV.

Example 5

Preparation of V

A 22 L reaction flask was charged with DMF (8 L), potassium carbonate (1576 g, 11.4 mol), and acetohydroxamic acid (428 g, 5.7 mol) and stirred at rt. Water (1.2 L, note: For Batch 1, 0.8 L of water was first added and an additional 0.4 L of water was added after stirring at rt for 27 h) was added slowly while keeping the reaction temperature at 20–30° C. After the reaction mixture was stirred for 30 min at 20–30° C., IV (1200 g, 1.9 mol) was added. The reaction mixture was stirred at rt for 4 to 20 h. This reaction mixture was quenched into 12 L of water in a 40 L reactor with vigorous agitation. The resulting slurry was stirred at rt for 2 h and then at 2–10° C. for another 1 h. The solid was filtered with a Dacron filter cloth. The cake was washed with cold water (8 L) and followed by cold acetonitrile (2 L) and dried in a vacuum oven to constant weight to give a crude product (1012 g). The crude product was dissolved in 12.5 L of acetonitrile at 65–80° C. After the solution was cooled to 25–37° C., water (2 L) was added over 2 h period while allowing the pot to cool to rt. The formed slurry was stirred at rt for 1 h. After cooling to 2–10° C., the solid was filtered with a Dacron filter cloth. The cake was washed with cold acetonitrile (4–6 L) and dried in a vacuum oven to constant weight to give the product V (92.3 g, 89%). HRMS for $C_{24}H_{21}F_4O_2N_8$ $(M+H)^+$ calcd 529.1724, found 529.1722. $^1$H-NMR (300 MHz, DMSO-$d_6$) 2.09 (6H), 3.29 (2H), 6.54 (2H), 6.96 (1H), 7.41–7.75 (7H), 8.06 (1H), 10.65 (1H). $^{19}$F-NMR −119.632 (1F), −61.257 (3F)

Example 6

Preparation of I

A 22 L reaction flask with overhead stirring, water condenser, and temperature probe was charged with ethanol (10 L) and V (monohydrate form, 850 g, 1.56 mol). The reaction mixture was heated to 65 to 80° C. to give a clear solution. After cooling to about 55° C., the warm solution was filtered through a cartridge filter. After transferring the filtrate back to the clean 22 L reactor and cooling the solution to 20–37° C., 4.6N HCl in IPA solution (355 mL, 1.63 mol) was charged through an addition funnel. After a slurry was formed, the mixture was stirred at rt for 1 h, and then at 2–8° C. for another 1 h. The solid was collected in a Buchner funnel with Dacron filter cloth. The cake was washed with cold ethanol (2 L) and followed by tert-butyl methyl ether (6 L), dried in a vacuum oven at 50° C. to give the product I (858 g, 98%). M.p. 258 C (dec). $^1$H-NMR (300 MHz, DMSO-$d_6$) 1.02 (ethanol), 2.74 (6H), 3.40 (ethanol), 4.35 (2H), 6.59(2H), 7.18 (1H), 7.34–7.80 (7H), 8.09 (1H), 10.99 (1H). $^{19}$F-NMR −118.174 (1F), −61.229 (3F).

Example 7

Preparation of Va

To a solution of V (5.06 g) in chloroform (40 mL) and methanol (120 mL) was added 35% $H_2O_2$ (20 mL) at rt. The reaction mixture was stirred at rt over 66 h. Water (180 mL) was then added to the reaction mixture and the resulting slurry was stirred at rt for 30 min. The solid was collected by filtration and dried in vacuo with nitrogen purge at rt to a constant weight (3.97 g).

Utility

The novel compounds of the present invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Compounds tested in the above assay are considered to be active if they exhibit a $K_i$ of $\leq 10 \mu M$. Preferred compounds of the present invention have $K_i$'s of $\leq 1 \mu M$. More preferred compounds of the present invention have $K_i$'s of $\leq 0.1 \mu M$. Even more preferred compounds of the present invention have $K_i$'s of $<0.01 \mu M$. Still more preferred compounds of the present invention have $K_i$'s of $\leq 0.001 \mu M$. Using the methodology described above, a number of compounds of the present invention were found to exhibit a $K_i$ of $\leq 10 \mu M$, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than $15 \mu m$, thereby confirming the utility of the compounds of the present invention as effective Xa inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but no compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Numerous modifications and variations of the present invention are possible in light of the above teachings. It is therefore to be understood that within the scope of the appended claims, the invention may be practiced otherwise than as specifically described herein.

What is claimed is:

1. A process for making a compound of Formula I:

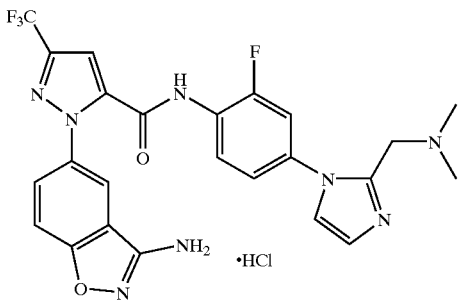

comprising:
(c) contacting a compound of Formula IVa with maleic acid to form a compound of Formula IV;

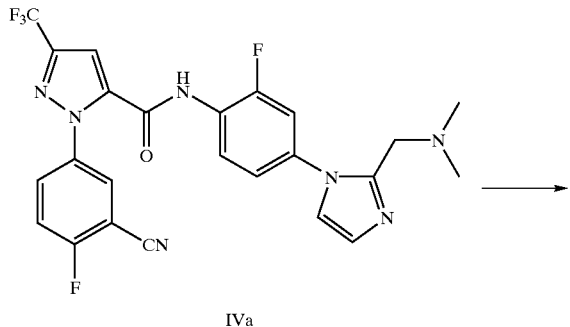

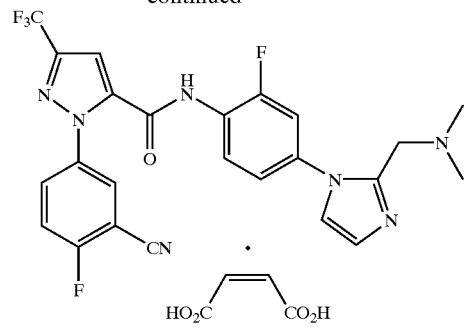

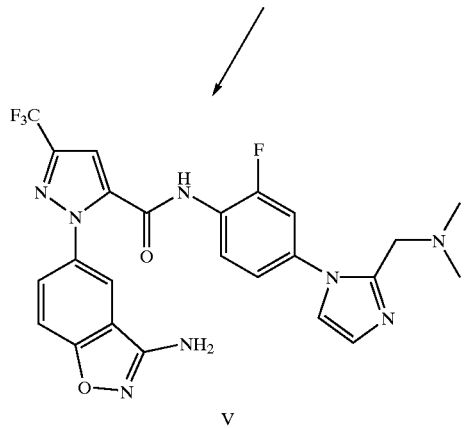

(d) converting a compound of Formula IV to a compound of Formula V; and,
(e) forming a compound of Formula I, wherein I is a mono-HCl salt or crystalline form or solvate thereof.

2. A process according to claim 1, wherein in (c), contacting with maleic acid is performed in the presence of a first solvent, ethyl acetate.

3. A process according to claim 2, wherein in (c), a second solvent, 1-chlorobutane, is added to enhance precipitation.

4. A process according to claim 1, wherein (d) is performed by contacting a compound of Formula IV with $HONHCOCH_3$ in the presence of a base and a solvent.

5. A process according to claim 4, wherein the base is selected from $K_2CO_3$, $Na_2CO_3$, $KHCO_3$, $NaHCO_3$, KF, NaOH, and KOH.

6. A process according to claim 5, wherein the base is $K_2CO_3$.

7. A process according to claim 4, wherein in (d), the solvent is selected from DMSO, DMAC, N-methylpyrrolidinone, and DMF.

8. A process according to claim 7, wherein in (d), the solvent is DMF, comprising:
0.5 to 50% by volume of water.

9. A process according to claim 7, wherein in (d), the solvent is DMF, comprising:
10, 11, 12, 13, 14, to 15% by volume of water.

10. A process according to claim 7, wherein in (d), the solvent is DMF, comprising:
15% by volume of water.

11. A process according to claim 1, wherein (e) is performed by contacting a compound of Formula V with HCl in a solvent selected from methanol, acetonitrile, isopropyl alcohol, ethanol, propanol, acetone, methyl isobutyl ketone (MIBK), 2-butanone, and water.

12. A process according to claim 11, wherein (e) is performed by contacting a compound of Formula V with HCl in ethanol.

13. A process according to claim 1, wherein the compound of Formula I is crystalline.

14. A process according to claim 1, wherein the compound of Formula I is a solvate selected from ethanol, propanol, isopropanol, acetone, MIBK, 2-butanone, and water.

15. A process according to claim 14, wherein the compound of Formula I is an ethanol solvate.

16. A compound of Formula I:

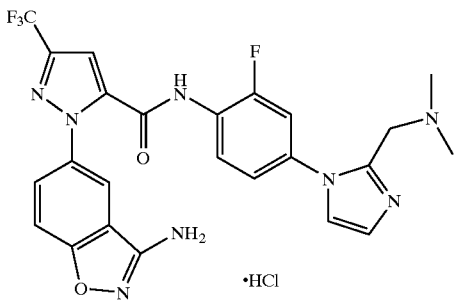

wherein I is a mono-HCl salt or crystalline form or solvate thereof.

17. A compound according to claim 16, wherein the compound of Formula I is crystalline.

18. A compound according to claim 16, wherein the compound of Formula I is a solvate selected from ethanol, propanol, isopropanol, acetone, MIBK, 2-butanone, and water.

19. A compound according to claim 18, wherein the compound of Formula I is an ethanol solvate.

20. A pharmaceutical composition, comprising:
a pharmaceutically acceptable carrier and a therapeutically effective amount of a compound according to claim 16 or a pharmaceutically acceptable salt thereof.

21. A method for treating a thromboembolic disorder, comprising:
administering to a patient in need thereof a therapeutically effective amount of a compound of claim 16 or a pharmaceutically acceptable salt thereof.

22. A pharmaceutical composition, comprising:
a pharmaceutically acceptable carrier and a therapeutically effective amount of a compound according to claim 17 or a pharmaceutically acceptable salt thereof.

23. A pharmaceutical composition, comprising:
a pharmaceutically acceptable carrier and a therapeutically effective amount of a compound according to claim 18 or a pharmaceutically acceptable salt thereof.

24. A pharmaceutical composition, comprising:
a pharmaceutically acceptable carrier and a therapeutically effective amount of a compound according to claim 19 or a pharmaceutically acceptable salt thereof.

25. The method according to claim 21, wherein the thromboembolic disorder is selected from an arterial cardiovascular thromboembolic disorder, an arterial cerebrovascular thromboembolic disorder, a venous cardiovascular thromboembolic disorder, and a venous cerebrovascular thromboembolic disorder.

26. The method according to claim 25, wherein the disorder is selected from unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

27. A method for treating a thromboembolic disorder, comprising:
administering to a patient in need thereof a therapeutically effective amount of a compound of claim 25 or a pharmaceutically acceptable salt thereof.

28. The method according to claim 27, wherein the thromboembolic disorder is selected from an arterial cardiovascular thromboembolic disorder, an arterial cerebrovascular thromboembolic disorder, a venous cardiovascular thromboembolic disorder, and a venous cerebrovascular thromboembolic disorder.

29. The method according to claim 28, wherein the disorder is selected from unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

30. A method for treating a thromboembolic disorder, comprising:
administering to a patient in need thereof a therapeutically effective amount of a compound of claim 18 or a pharmaceutically acceptable salt thereof.

31. The method according to claim 30, wherein the thromboembolic disorder is selected from an arterial cardiovascular thromboembolic disorder, an arterial cerebrovascular thromboembolic disorder, a venous cardiovascular thromboembolic disorder, and a venous cerebrovascular thromboembolic disorder.

32. The method according to claim 31, wherein the disorder is selected from unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

33. A method for treating a thromboembolic disorder, comprising:
administering to a patient in need thereof a therapeutically effective amount of a compound of claim 19 or a pharmaceutically acceptable salt thereof.

34. The method according to claim 33, wherein the thromboembolic disorder is selected from an arterial cardiovascular thromboembolic disorder, an arterial cerebrovascular thromboembolic disorder, a venous cardiovascular thromboembolic disorder, and a venous cerebrovascular thromboembolic disorder.

35. The method according to claim 34, wherein the disorder is selected from unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

* * * * *

UNITED STATES PATENT AND TRADEMARK OFFICE
CERTIFICATE OF CORRECTION

PATENT NO. : 6,667,332 B2
DATED : December 23, 2003
INVENTOR(S) : Li et al.

It is certified that error appears in the above-identified patent and that said Letters Patent is hereby corrected as shown below:

Title page,
Item [73], Assignee: should read -- Bristol-Myers Squibb Pharma Company --
Item [75], Inventors, should read Applicants:
-- Hui-Yin Li
  Luigi Anzalone
  Fuqiang Jin
  David J Meloni
  Jung-Hui Sun
  Lucius T Rossano
  Christopher A Teleha
  Jiacheng Zhou
  Thomas E Smyser --

Signed and Sealed this

Fourth Day of May, 2004

JON W. DUDAS
*Acting Director of the United States Patent and Trademark Office*